United States Patent [19]

Hoeksema et al.

[11] 4,107,296

[45] Aug. 15, 1978

[54] ANTIBIOTIC RUBRADIRIN C

[75] Inventors: Herman Hoeksema, Kalamazoo; Fritz Reusser, Portage, both of Mich.

[73] Assignee: The Upjohn Company, Kalamazoo, Mich.

[21] Appl. No.: 810,955

[22] Filed: Jun. 29, 1977

[51] Int. Cl.² .............................................. A61K 35/00
[52] U.S. Cl. ..................................... 424/121; 424/124
[58] Field of Search ........................................ 424/121

[56] References Cited

U.S. PATENT DOCUMENTS

| | | | |
|---|---|---|---|
| 3,335,057 | 8/1967 | Johnson et al. | 424/119 |
| 4,032,631 | 6/1977 | Celmer et al. | 424/121 |

*Primary Examiner*—Jerome D. Goldberg
*Attorney, Agent, or Firm*—Roman Saliwanchik

[57] ABSTRACT

Antibiotic rubradirin C producible by the controlled fermentation of the known microorganism *Streptomyces achromogenes* var. *rubradiris,* NRRL 3061. This antibiotic and its base-addition salts are active against *Streptococcus pyogenes* and *Bacillus cereus.* Accordingly, they can be used in various environments to eradicate or control such microorganisms.

4 Claims, 2 Drawing Figures

ANTIBIOTIC RUBRADIRIN C

BACKGROUND OF THE INVENTION

Antibiotic rubradirin, and a microbiological process for its preparation, are disclosed in U.S. Pat. No. 3,335,057. Rubradirin B is disclosed in U.S. application Ser. No. 787,833, filed Apr. 15, 1977. Degradation products of rubradirin and rubradirin B, and processes for their preparation are disclosed in U.S. application Ser. No. 793,785, filed May 5, 1977.

BRIEF SUMMARY OF THE INVENTION

The novel antibiotic of the invention, rubradirin C, is obtained by culturing *Streptomyces achromogenes* var. *rubradiris*, NRRL 3061, in an aqueous nutrient medium under aerobic conditions. The fermentation conditions disclosed in U.S. Pat. No. 3,335,057, referred to above, can be used to prepare rubradirin C. However, the fermentation procedures disclosed herein are preferred for the preparation of rubradirin C.

DETAILED DESCRIPTION OF THE INVENTION

Chemical and Physical Properties of Rubradirin C

Molecular Weight: 779 (determined by field desorption mass spectroscopy).

Elemental Analysis: Calculated for $C_{40}H_{33}N_3O_{14}$: C, 61.61; H, 4.26; N, 5.39. Found: C, 60.77; H, 4.45; N, 5.10.

Melting Point: >300° Dec.

Ultraviolet Absorption Spectrum

Figure 2:
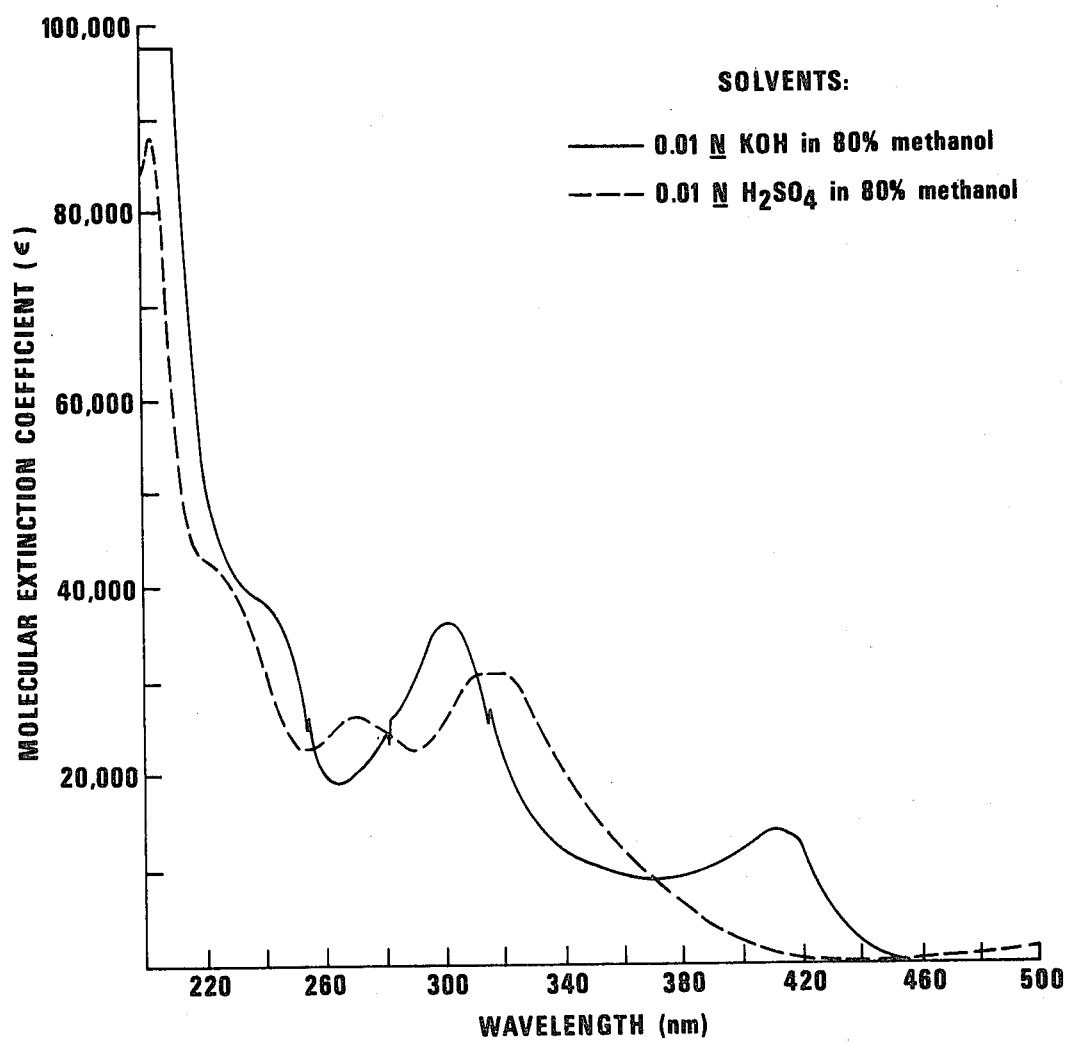

The ultraviolet absorption maxima of rubradirin C, as reproduced in FIG. 2 of the drawings are: In 0.01 N KOH in 80% methanol, λ, a, (ε): 420 sh, 16.0, (12,500); 410, 18.10, (14,1000); 302, 45.92. (35,818); 238 sh, 49.12, (38.313).

In 0.01 N $H_2SO_4$ in 80% methanol, λ, a, (ε): 320, 38.97, (30,400); 310 sh; 271, 33.64, (26,239); 220, 53.39, (41,644); 203, 110.52, (86,205).

Infrared Absorption Spectrum

Figure 1:
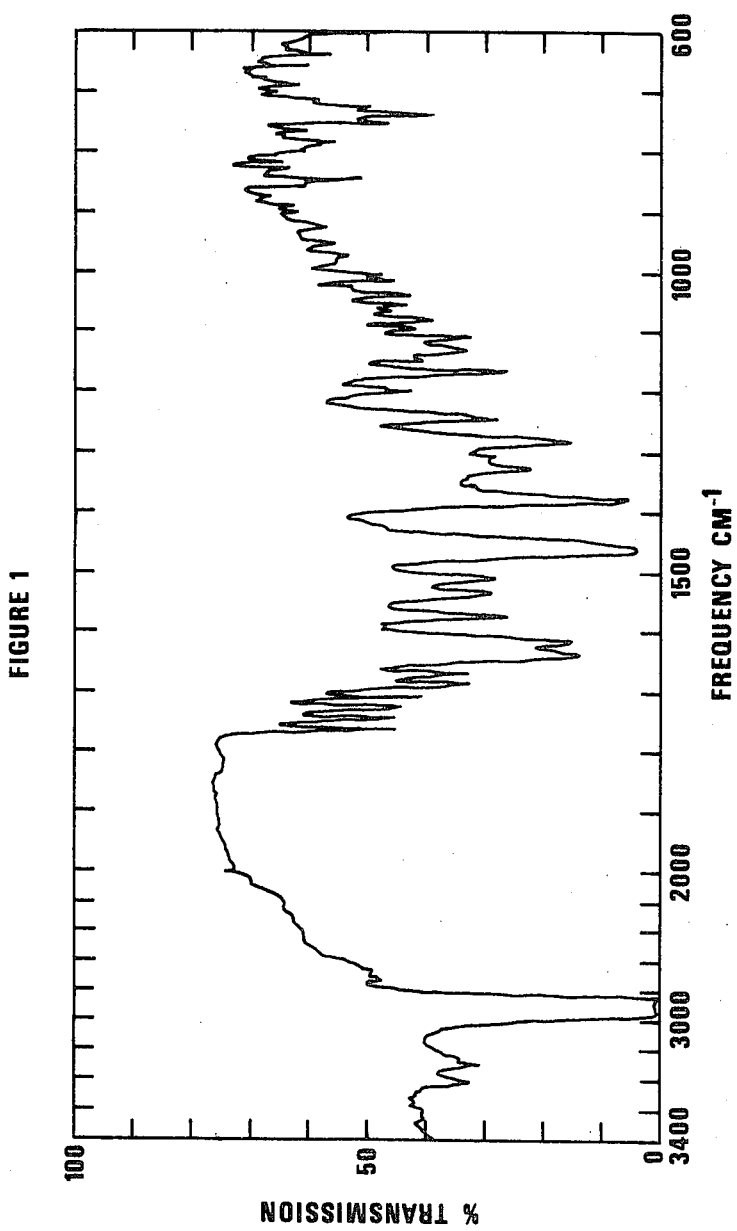

Rubradirin C has a characteristic infrared absorption spectrum in a mineral oil mull as shown in FIG. 1 of the drawings. Peaks are observed at the following wave lengths expressed in reciprocal centimeters:

| Band Frequency (Wave Numbers) | Intensity |
| --- | --- |
| 3650 | M |
| 3600 | M |
| 3410 | M |
| 3280 | M |
| 2930 | S |
| 2850 | S |
| 2720 | M |
| 2665 | M |
| 1758 | M |
| 1740 | M |
| 1720 | M |
| 1705 | M |
| 1684 | M |
| 1665 | M |
| 1635 | S |
| 1615 | S |
| 1570 | S |
| 1531 | M |
| 1508 | M |
| 1462 | S |
| 1377 | S |
| 1365 | S, sh (sh=shoulder) |
| 1329 | S |
| 1303 | M |

-continued

| Band Frequency (Wave Numbers) | Intensity |
| --- | --- |
| 1280 | S |
| 1240 | M |
| 1205 | W, sh |
| 1195 | M |
| 1164 | S |
| 1140 | M |
| 1127 | M |
| 1106 | M |
| 1090 | M |
| 1076 | M |
| 1060 | M |
| 1050 | M |
| 1040 | M |
| 1023 | M |
| 1008 | M |
| 1000 | M |
| 980 | W |
| 970 | W |
| 948 | W |
| 920 | W |
| 895 | W |
| 885 | W |
| 868 | W |
| 835 | M |
| 823 | W |
| 810 | W |
| 779 | W |
| 757 | W |
| 745 | M |
| 735 | M |
| 720 | M |
| 708 | W |
| 695 | W |
| 683 | W |
| 670 | W |
| 650 | W |
| 637 | W |

Key: S=Strong M=Medium and W=Weak

Solubilities

The novel compound of the invention is soluble in aqueous bases above pH 7.5, and insoluble in water below pH 6.0. It is also soluble in lower alkyl amides such as dimethylformamide and dimethylacetamide, dimethylsulfoxide, and ethyl acetate which is saturated with water. It is very slightly soluble in lower alcohols (methanol and ethanol), chloroform, and tetrahydrofuran. It is insoluble in hydrocarbon solvents such as benzene, toluene, and the alkanes (pentane through the higher alkanes).

Antibacterial Spectrum of Rubradirin C

Rubradirin C is antibacterially active against the following microorganisms on a standard disc plate assay (12.7 mm assay discs).

| Microorganism | BU/mg |
| --- | --- |
| *Streptococcus pyogenes* | 4 |
| *Bacillus cereus* | <1 |

A unit volume (0.08 ml) of solution containing the substance to be assayed is placed on a 12.7 mm paper disc which is then placed on an agar plate seeded with the assay organism. The agar plate is then incubated for 16 to 18 hours at 37° C. A biounit (BU) is defined as the concentration of the antibiotic which gives a 20 mm zone of inhibition under the standard assay conditions. Thus, if for example a fermentation beer has to be diluted 1/100 to give a 20 mm zone of inhibition, the potency of such beer is 100 BU/ml.

THE MICROORGANISM

The microorganism used for the production of rubradirin C is the known microorganism *Streptomyces*

*achromogenes* var. *rubradiris*, NRRL 3061. This culture is available to the public upon request to the culture repository at Peoria, Illinois. The characteristics of this culture are disclosed in U.S. Pat. No. 3,335,057, Columns 2–4.

The new compound of the invention is produced when the elaborating organism is grown in an aqueous nutrient medium under submerged aerobic conditions. It is to be understood also that for the preparation of limited amounts surface cultures in bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, corn starch, lactose, dextrin, molasses, and the like. Preferred nitrogen sources include corn steep liquor, yeast, autolyzed brewer's yeast with milk solids, soybean meal, cottonseed meal, corn meal, milk solids, pancreatic digest of casein, distiller's solubles, animal peptone liquors, meat and bone scraps, and the like. Combination of these carbon and nitrogen sources can be used advantageously. Trace metals, for example, zinc, magnesium, manganese, cobalt, iron, and the like need not be added to the fermentation media since tap water and unpurified ingredients are used as media components. Production of the compound of the invention can be effected at any temperature conducive to satisfactory growth of the microorganism, for example, between about 18° and 40° C. and preferably between about 26° and 30° C. Ordinarily, optimum production of the compound is obtained in about 2 to 10 days. The medium normally stays fairly close to neutral, or on the alkaline side during the fermentation. The final pH is dependent, in part, on the buffers present, if any, and in part on the initial pH of the culture medium which is advantageously adjusted to about pH 6–8 prior to sterilization.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating the broth culture with an aliquot from a soil or slant culture. When a young, active, vegetative inoculum has thus been secured, it is transferred aseptically to large vessels or tanks. The medium in which the vegetative inoculum is produced can be the same as, or different from, that utilized for the production of the new compound, as long as it is such that a good growth of the microorganism is obtained.

A variety of procedures can be employed in the isolation and purification of rubradirin C, for example, solvent extraction, liquid-liquid distribution in a Craig apparatus, the use of adsorbents, precipitation from beer at acid pH, and crystallization from solvents. Acid precipitation procedures are preferred for recovery inasmuch as they are less time consuming and less expensive, and higher recovery yields are obtained thereby.

In a preferred process, rubradirin C is recovered from its culture medium by separation of the mycelia and undissolved solids by conventional means such as by filtration or centrifugation. The antibiotic is then removed from the filtered beer by adjusting the pH to about 4.0 with sulfuric acid. The precipitate which forms is removed by filtration, using a filter aid such as Dicalite. The cake is then eluted with acetone or ethyl acetate. The cake eluates are concentrated to an aqueous mixture and freeze-dried. The dried material is leached with acetone or ethyl acetate and the solvent phase is concentrated, then diluted with four volumes of Skellysolve B (isomeric hexanes). The rubradirin complex is filtered off and dried.

Crude preparations of rubradirin C can be subjected to silica gel chromatography to obtain essentially pure rubradirin C. A suitable solvent system in this procedure can be chloroform:methanol (99:1 v/v).

Salts of rubradirin C are formed employing the free acid of rubradirin C and an inorganic or organic base. The rubradirin C salts can be prepared as for example by suspending rubradirin C free acid in water, adding a dilute base until the pH of the mixture is about 7 to 8, and freeze-drying the mixture to provide a dried residue consisting of the rubradirin C salt. Rubradirin C salts which can be formed include the sodium, potassium, and calcium. Other salts of rubradirin C including those with organic bases such as primary, secondary, and tertiary mono-, di-, and poly- amines can also be formed using the above-described or other commonly employed procedures.

The new compound of the invention, rubradirin C, inhibits the growth of the following organisms: *Streptococcus pyogenes* and *Bacillus cereus*. Since rubradirin C is active against *B. cereus*, it can be used to treat woolen felts which are a well-known source of contamination by *B. cereus* in the paper industry. Further, rubradirin C, or its salts, can be used as an industrial preservative, for example, as a bacteriostatic rinse for laundered clothes and for impregnating paper and fabrics; and, it is useful for suppressing the growth of sensitive organisms in plate assays and other microbiological media.

The following examples are illustrative of the process and products of the present invention, but are not to be construed as limiting. All percentages are by weight, and solvent mixture proportions are by volume unless otherwise noted.

EXAMPLE 1

A. Fermentation

An agar slant of *Streptomyces achromogenes* var. *rubradiris*, NRRL 3061, is used to inoculate a series of 500-ml Erlenmeyer flasks each containing 100 ml of sterile seed medium consisting of the following ingredients:

| | |
|---|---|
| Glucose monohydrate | 25 g/liter |
| Pharmamedia* | 40 g/liter |
| Tap water q.s. | 1 liter |

Pharmamedia is an industrial grade of cottonseed flour produced by Traders Oil Mill Company, Fort Worth, Texas.

The flasks are incubated for 3 days at 28° C. on a Gump rotary shaker operating at 250 r.p.m.

Seed inoculum (5%), prepared as described above, is used to inoculate a series of 500-ml Erlenmeyer flasks each containing 100 ml of sterile fermentation medium consisting of the following ingredients:

| | |
|---|---|
| Starch | 10 g/liter |
| Corn steep liquor | 20 g/liter |
| Distillers' solubles | 15 g/liter |
| Mg (NO$_3$)$_2$ · 6H$_2$O | 3.8 g/liter |
| Tap water q.s. | 1 liter |

The fermentation medium presterilization pH is 7.2.

The fermentation flasks are incubated at 28° C. on a Gump rotary shaker operating at 250 r.p.m. The fermentation flasks are harvested after about 3 to 4 days.

B. Recovery

Whole broth from a fermentation, as described above, is slurried with 4 percent of its weight of diatomaceous earth and filtered. The filter cake is washed with 1/10 volume of water and the wash is added to the clear beer. The clear beer is adjusted to pH 4.0 with 6 N sulfuric acid and filtered with the aid of Dicalite. The spent beer is discarded. The wet cake is leached with ethyl acetate and the solvent phase is then concentrated to an aqueous phase. The latter is freeze-dried. The residue is dissolved in ethyl acetate and diluted with 4 volumes of Skellysolve B. The precipitate which is collected and dried contains a mixture including rubradirin, rubradirin B and rubradirin C.

C. Purification

A two gram quantity of crude preparation containing rubradirin C, prepared as described above, is chromatographed on 500 g of silica gel G (70–230 mesh, E. Merck), buffered at pH 5.8 by pretreatment with 54.4 mg of $KH_2PO_4$ per gram of silica. A 500 g quantity of this silica, slurried in chloroform, is poured into a 2 inch (diameter) glass column and to this is added the two gram quantity of a crude preparation containing rubradirin C. The column is developed with chloroform and collection of 20 ml fractions is initiated when the first color band begins to elute. The antibiotic rubradirin, as shown by thin layer chromatography (tlc), is eluted from the column by the chloroform. After collection of 236 fractions, the eluant is changed to chloroform:methanol (99:1 v/v). Fractions 469 to 484 are found to contain 100 mg of essentially pure rubradirin C as shown by tlc. Rubradirin B is shown by tlc to be in fractions 464 to 468.

The tlc system consists of silica gel HF 254 buffered at pH 5.8 and developed with chloroform:methanol (99:1 v/v). Detection of the antibiotic is made by visual observation of the red color. The $R_f$ values for rubradirin, rubradirin B, and rubradirin C in this system are 0.66, 0.50, and 0.43, respectively.

The essentially pure rubradirin C, obtained as described above, is crystallized from dimethylsulfoxide-$d_6$.

EXAMPLE 2

Sodium Salt of Rubradirin C

Twenty-five mg of rubradirin C, as prepared in Example 1, is suspended in 2 ml of methanol. Add 2 equivalents (ca. 3.5 mg) of sodium methoxide in 1 ml of methanol. Then add ether to precipitate the sodium salt of rubradirin C.

We claim:

1. Essentially pure rubradirin C, a compound which
   (a) is effective in inhibiting the growth of *Streptococcus pyogenes* and *Bacillus cereus*;
   (b) is soluble in dimethylformamide, dimethylsulfoxide and aqueous base, and is insoluble in aqueous acid and hydrocarbon solvents;
   (c) has the following elemental analysis: C, 60.77; H, 4.45; N, 5.10;
   (d) has a molecular weight of 779 (determined by field desorption mass spectroscopy);
   (e) has a characteristic infrared absorption spectrum as shown in FIG. 1 of the accompanying drawings;
   (f) has a characteristic ultraviolet absorption spectrum as shown in FIG. 2 of the accompanying drawings;
   (g) has a melting point >300° Dec.; and,
   (h) has a molecular formula $C_{40}H_{33}N_3O_{14}$.

2. Rubradirin C, as defined in claim 1, in its crystalline form.

3. A compound selected from the group consisting of rubradirin C, according to claim 1, and salts thereof with alkali metal or alkaline earth metals.

4. Sodium salt of rubradirin C, said rubradirin C defined in claim 1.

* * * * *